United States Patent
Fong

(10) Patent No.: US 8,273,036 B2
(45) Date of Patent: Sep. 25, 2012

(54) WEARABLE PORTABLE DEVICE FOR INCREASING USER AWARENESS OF A PARETIC LIMB AND RECORDING THE USER AWARENESS

(75) Inventor: Nai Kuen Fong, Hong Kong (HK)

(73) Assignee: The Hong Kong Polytechnic University, Kowloon (HK)

( * ) Notice: Subject to any disclaimer, the term of this patent is extended or adjusted under 35 U.S.C. 154(b) by 698 days.

(21) Appl. No.: 12/344,102

(22) Filed: Dec. 24, 2008

(65) Prior Publication Data

US 2010/0160834 A1    Jun. 24, 2010

(51) Int. Cl.
*A61B 5/117* (2006.01)
*A61B 5/103* (2006.01)

(52) U.S. Cl. ........................ 600/595

(58) Field of Classification Search .............. 600/300, 600/301, 557, 587, 595; 463/37; 33/512; 455/404.1, 404.2, 456.1
See application file for complete search history.

(56) References Cited

U.S. PATENT DOCUMENTS

| 6,212,135 B1 | 4/2001 | Schreiber |
| 2003/0030544 A1 | 2/2003 | Smith |
| 2011/0040204 A1* | 2/2011 | Ivorra et al. ............... 600/557 |

OTHER PUBLICATIONS

Van Hulle, A. & Hux, K. (2006). Improvement patterns among survivors of brain injury: Three examples documenting the effectiveness of memory compensation strategies. Brain Injury, 20(1), 101-9.

Nieuwboer, A., Kwakkel, G., Rochester, L., Jones, D., van Wegen, E., Willems, A. M., Chavret, F., Hetherington, V., Baker, K., & Lim, I. (2007). Cueing training in the home improves gait-related mobility in Parkinson's disease: The RESCUE trial. Journal of Neurology, Neurosurgery, and Psychiatry, 78, 134-140.
Schwartz et al. (1999). Ipsilesional intention neglect and the effect of cueing. Neurology, 53, 2017.
Pollack, M.E. (2005). Intelligent technology for an aging population. AI Magazine, 9-24.
Robertson, I.H., North, N.T., Geggie, C. (1992). Spatiomotor cueing in unilateral left neglect: Three case studies of its therapeutic effects. Journal of Neurology, Neurosurgery, and Psychiatry, 55, 799-805.
Robertson, I. H., & North, N. (1992). Spatial-motor cueing in unilateral neglect: The role of hemispace, hand and motor activation. Neuropsychologia, 30(6), 553-563.
Robertson, I.H., Hogg, K., McMillan, T.M. (1998). Rehabilitation of unilateral neglect: Improving function by contralesional limb activation. Neuropsychological Rehabilitation, 8, 19-29.

(Continued)

*Primary Examiner* — Brian Szmal
(74) *Attorney, Agent, or Firm* — Muncy, Geissler, Olds & Lowe, PLLC

(57) ABSTRACT

A wearable portable device (10) for increasing user awareness of a paretic limb and recording the user awareness, the device (10) comprising: a sensory signal generator (52, 20) to emit a continuous sensory signal to remind the user to move the paretic limb according to a predetermined schedule; a switch (13) to be actuated by the user for stopping the emission of the sensory signal; and an accelerometer (61) to detect movement of the paretic limb in 3-axis; wherein after the switch (13) is actuated by the user, the user is instructed to move the paretic limb in accordance with predetermined instructions and the movement of the paretic limb detected by the accelerometer (61) and response time of when the switch (13) is actuated after the sensory signal is emitted are recorded for analysis by data analysis software.

14 Claims, 10 Drawing Sheets

OTHER PUBLICATIONS

Maddicks, R., Marzillier, S.L., Parker, G. (2003). Rehabilitation of unilateral neglect in the acute recovery stage: The efficacy of limb activation therapy. Neuropsychological Rehabilitation, 13(3), 391-408.

Samuel, C. et al. (2000). Rehabilitation of very severe unilateral neglect by visuo-spatio-motor cueing: Two single case studies. Neuropsychological Rehabilitation, 10(4), 385-99.

Robertson, I.H. et al. (2002). Rehabilitation by limb activation training reduces left-sided motor impairment in unilateral neglect patients: A single-blind randomized control trial. Neuropsychological Rehabilitation, 12(5), 439-54.

O'Neill, B., & McMillan, T. M. (2004). The efficacy of contralesional limb activation in rehabilitation of unilateral hemiplegia and visual neglect: A baseline-intervention study. Neuropsychological Rehabilitation, 14(4), 437-447.

Haeuber, E. et al. (2004). Accelerometer monitoring of home and community based ambulatory activity after stroke. Archives of Physical Medicine and Rehabilitation, 85, 1997-2001.

Uswatte, G. et al. (2005). Ambulatory monitoring of arm movment using accelerometry: An objective measure of upper extremity rehabilitation in persons with chronic stroke. Archives of Physical Medicine and Rehabilitation, 86, 1498-501.

Uswatte, G. et al. (2006). Validity of accelerometry for monitoring real-world arm activity in patients with subacute stroke: Evidence from the extremity constraint-induced therapy evaluation trial. Archives of Physical Medicine and Rehabilitation, 87, 1340-5.

* cited by examiner

Figure 8

Sensory Cueing Wristwatch Configurator

81 — Vibration interval (minutes) [ 5 ]   [ Edit ]

82 — Epoch time (seconds) [ 2 ]

83 — Motion sampling rate (Hz) [ 10 ]   [ Accept ]

84 — Enable motion logging ✓

85 — Vibration patterns
Pattern On (sec) Off (sec)   [ Cancel ]

| Pattern | On (sec) | Off (sec) |
|---|---|---|
| 1 | 5 | 5 |
| 2 | 1 | 1 |
| 3 | 3 | 1 |
| 4 | 1 | 3 |
| 5 | 3 | 3 |

[ Exit ]

WEARABLE PORTABLE DEVICE FOR INCREASING USER AWARENESS OF A PARETIC LIMB AND RECORDING THE USER AWARENESS

TECHNICAL FIELD

The invention concerns a wearable portable device for increasing user awareness of a paretic limb and recording the user awareness.

BACKGROUND

Stroke is the fourth leading cause of death, and the most significant cause of severe disability, in Hong Kong. It affects 3.6 per 1000 people per year. Unilateral neglect (UN) is a common phenomenon for hemiplegia in stroke patients which can be attributed to lack of arousal or spatial attention over the contralesional side. UN occurs in about 20% of stroke patients.

Studies show that sensory stimulation to the hemiplegic side is an effective treatment and practice. Traditionally, sensory stimulation was provided to patients manually by professional therapists. This is time-consuming and laborious for the therapists.

Two kinds of approach have accounted for a variety of neglect treatments including: the recruitment hypothesis that comprises treatments targeting spatial representation deficits; and the cueing hypothesis that comprises treatments targeting arousal deficits and deficient visual attention. In a single case study, spatial bias in unilateral neglect can briefly be reduced using self-initiated exogenous loud voice stimuli.

Therefore there is a desire for a device which enables daily autonomous practicing to treat users suffering unilateral neglect.

SUMMARY OF THE INVENTION

In a first preferred aspect, there is provided a wearable portable device for increasing user awareness of a paretic limb and recording the user awareness, the device comprising:
- a sensory signal generator to emit a continuous sensory signal to remind the user to move the paretic limb according to a predetermined schedule;
- a switch to be actuated by the user for stopping the emission of the sensory signal; and
- an accelerometer to detect movement of the paretic limb in 3-axis;
- wherein after the switch is actuated by the user, the user is instructed to move the paretic limb in accordance with predetermined instructions and the movement of the paretic limb detected by the accelerometer and response time of when the switch is actuated after the sensory signal is emitted are recorded for analysis by data analysis software.

The device may further comprise a memory to store the recorded movement, time of movement, time of emission of the sensory signal, and time of actuation of the switch, for subsequent processing by the data analysis software.

The sensory signal may be a vibration output, audio output, visual output or a combination thereof.

The device may be a wristwatch and further comprise an adjustable strap to fasten the device around the wrist of the user.

The data analysis software may analyse and interpret the recorded movement, time of movement, time of emission of the sensory signal, and time of actuation of the switch, and generates charts to illustrate how much movement of the limb occurs in response to the sensory signal and how many times the limb is moved above a predetermined threshold during a predetermined time interval.

The device may further comprise rotary switches to enable the user to configure patterns, duration and intensity of the emission of the sensory signal.

The data analysis software may have a configuration tool to enable the user to set the parameters for the device including: vibration interval, epoch time, motion sampling rate, motion logging and vibration patterns.

The switch may be a substantially large button provided in a central location on an upper surface of the device.

The button may be at least semi-transparent to enable an LED backlight positioned beneath the button to generate a visual indication of the emission of the sensory signal.

The device may further comprise a memory slot for the memory.

The device may further comprise a rechargeable battery to provide electrical power for the device.

In a second aspect, there is provided a system for increasing user awareness of a paretic limb, the system comprising:
- a vibrating wrist-worn device which vibrates in order to remind the user to move the paretic limb according to a predetermined schedule, the device having a button to be pressed by the user for stopping the vibration, an accelerometer to detect movement of the paretic limb in 3-axis and the button is pressed by the user, the user is instructed to move the paretic limb in accordance with predetermined instructions;
- data analysis software to analyse the movement of the paretic limb detected by the accelerometer and response time of when the button is pressed after the vibration commences.

In a third aspect, there is provided a method for increasing user awareness of a paretic limb, the method comprising:
- generating a sensory signal to remind the user to move the paretic limb according to a predetermined schedule;
- actuating a switch by the user for stopping the emission of the sensory signal; and
- detect movement of the paretic limb in 3-axis;
- wherein after the switch is actuated by the user, the user is instructed to move the paretic limb in accordance with predetermined instructions and the movement of the paretic limb detected by the accelerometer and response time of when the switch is actuated after the sensory signal is emitted are recorded for analysis by data analysis software.

Sensory cueing can reduce the unilateral neglect for patients with neglect after intervention and continual follow-up. The effect of sensory cueing shows an increase in upper extremity movements especially with the forearm in response to sensory cueing for stroke patients with or without neglect.

BRIEF DESCRIPTION OF THE DRAWINGS

An example of the invention will now be described with reference to the accompanying drawings in which:

FIG. 8 is a screenshot from a data analysis software application to set parameters for the device of FIG. 1;

DETAILED DESCRIPTION OF THE DRAWINGS

Figure 1:
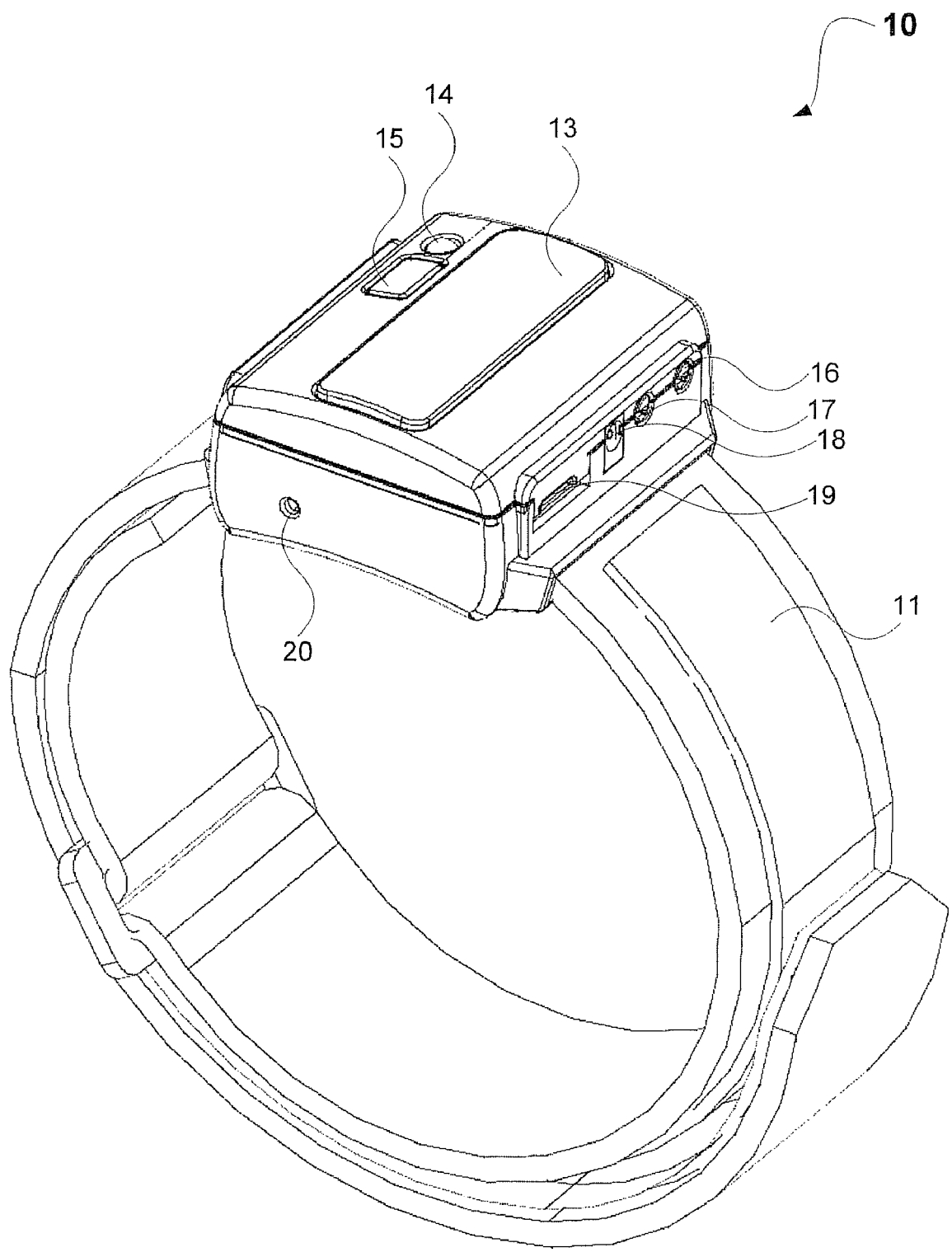
FIG. 1 is a perspective view from above of a wearable portable device in accordance with a preferred embodiment of the present invention.
Figure 2:
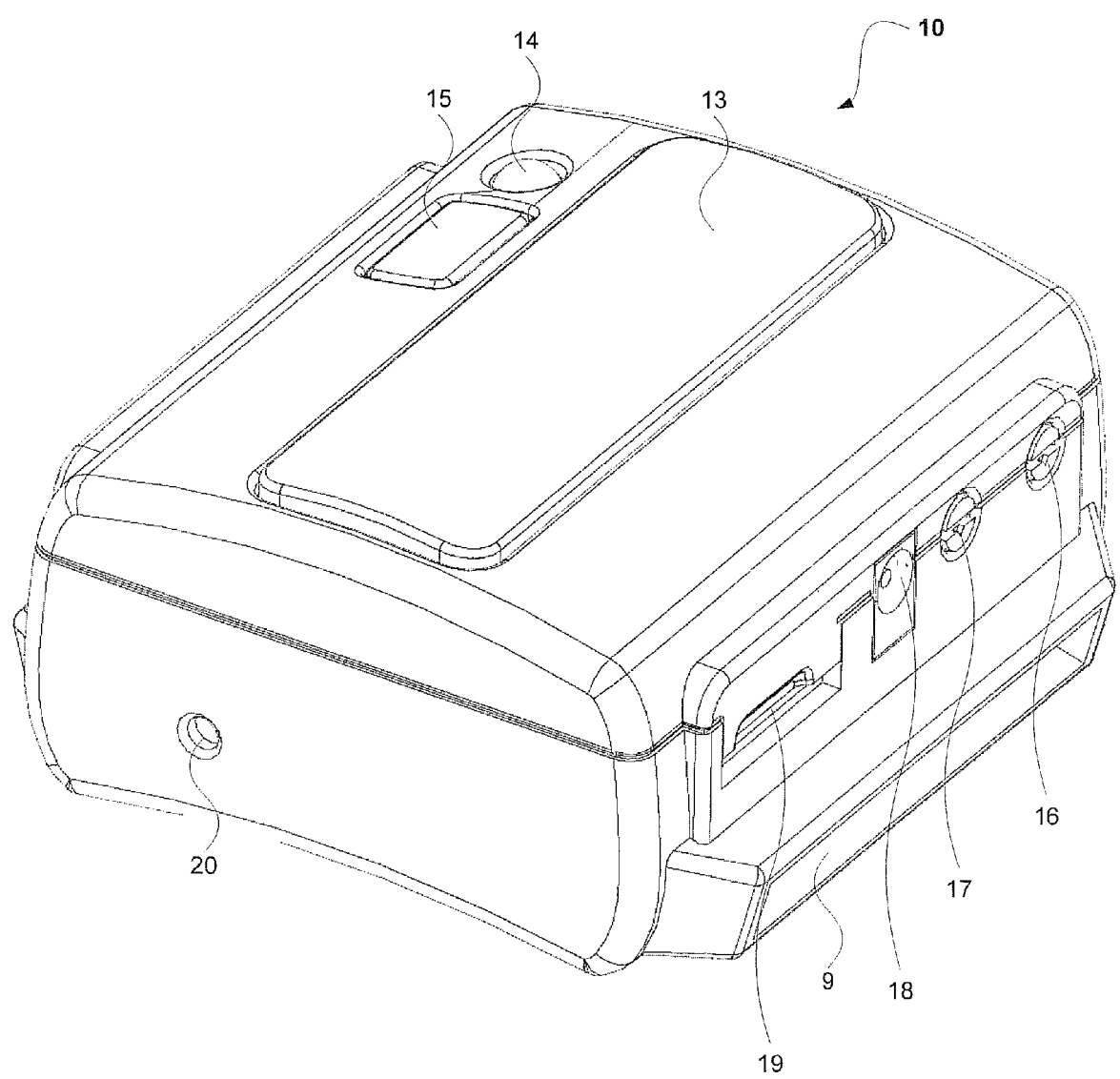
FIG. 2 is a perspective view from above of the device of FIG. 1 without a fastening strap.
Figure 3:
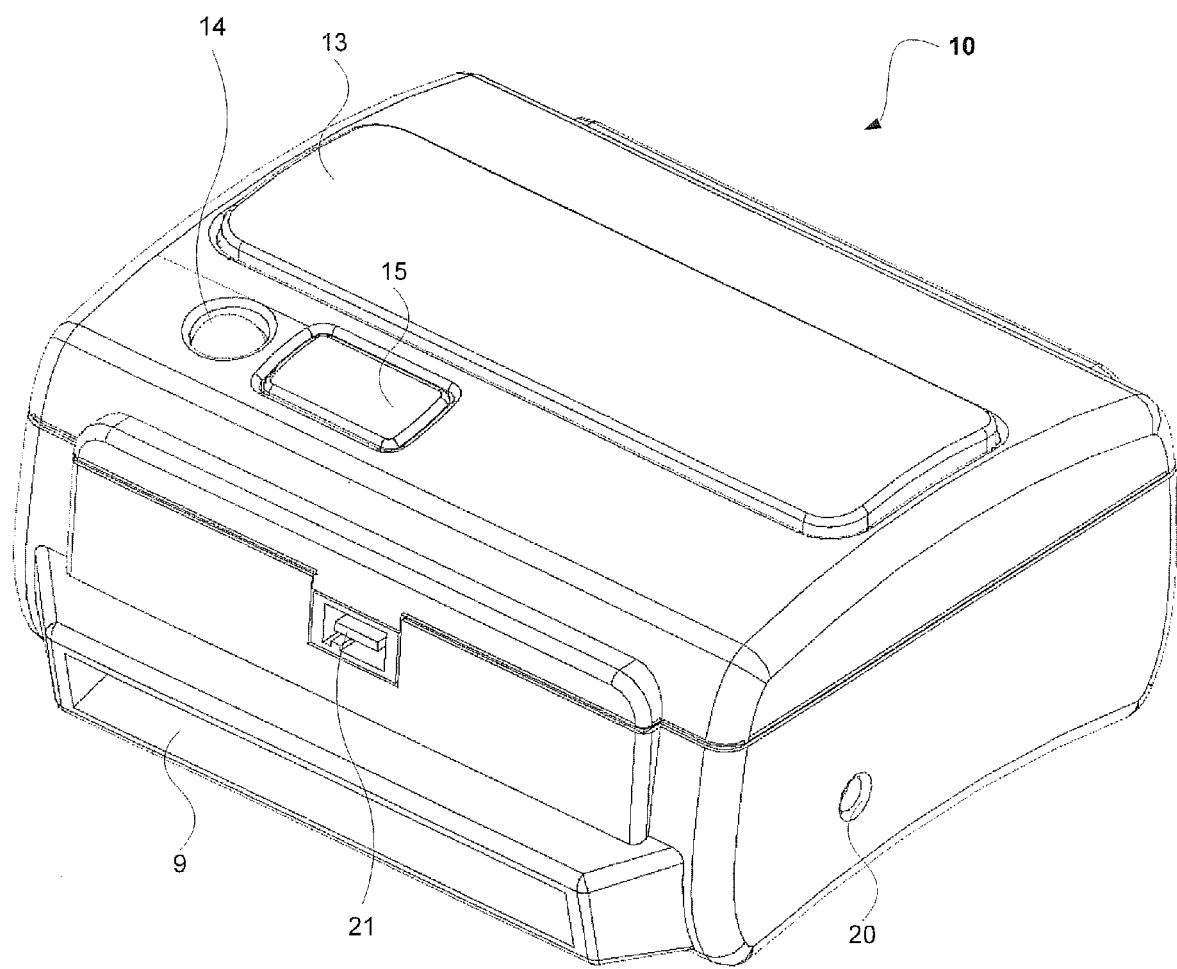
FIG. 3 is a perspective view from above of the device of FIG. 2 rotated 90° anti-clockwise.
Figure 4:
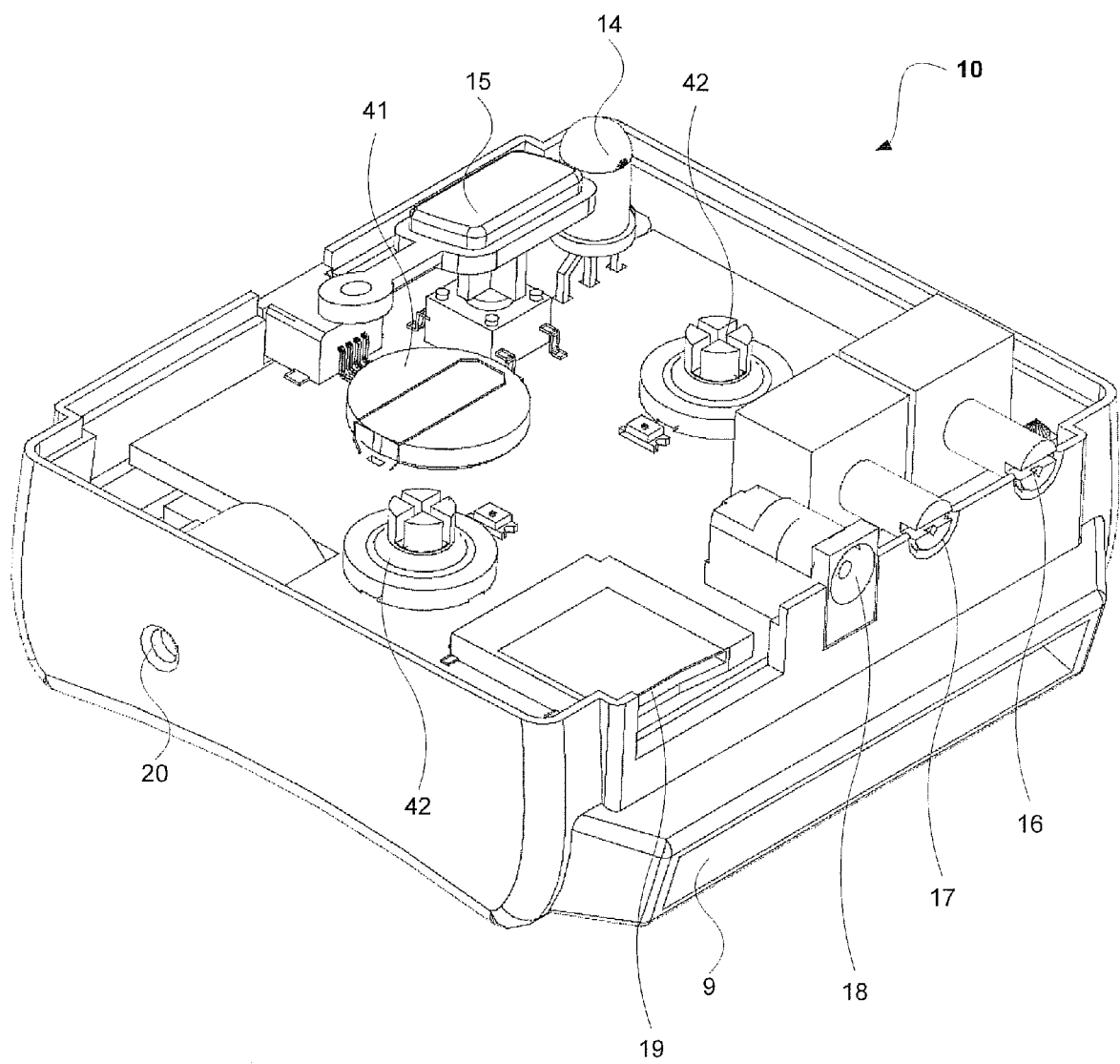
FIG. 4 is a perspective view from above of the device of FIG. 2 with a casing of the device removed to show the internal components of the device.
Figure 5:
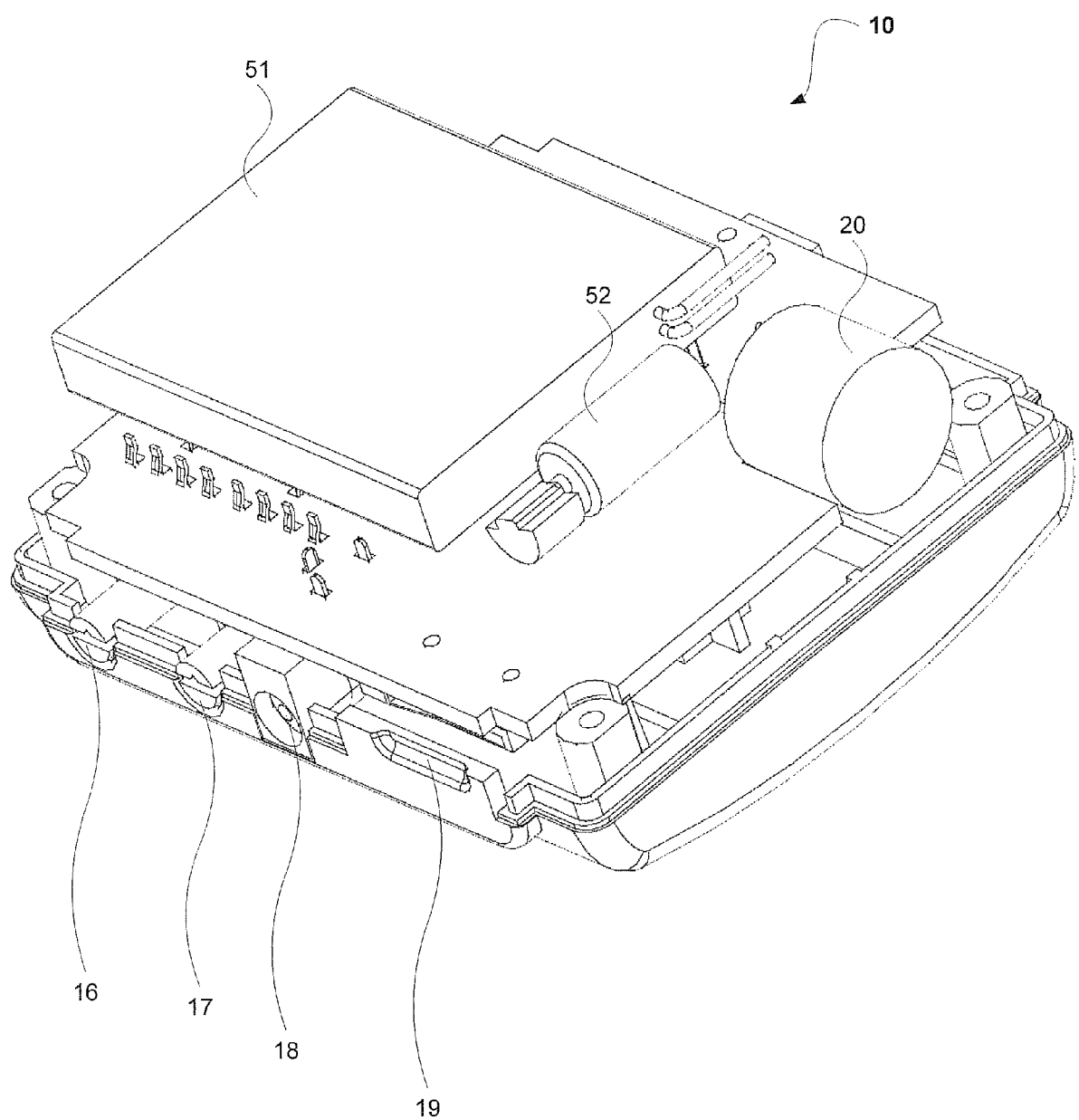
FIG. 5 is a perspective view from below of the device of FIG. 2 with the casing of the device removed to show the internal components of the device.
Figure 6:
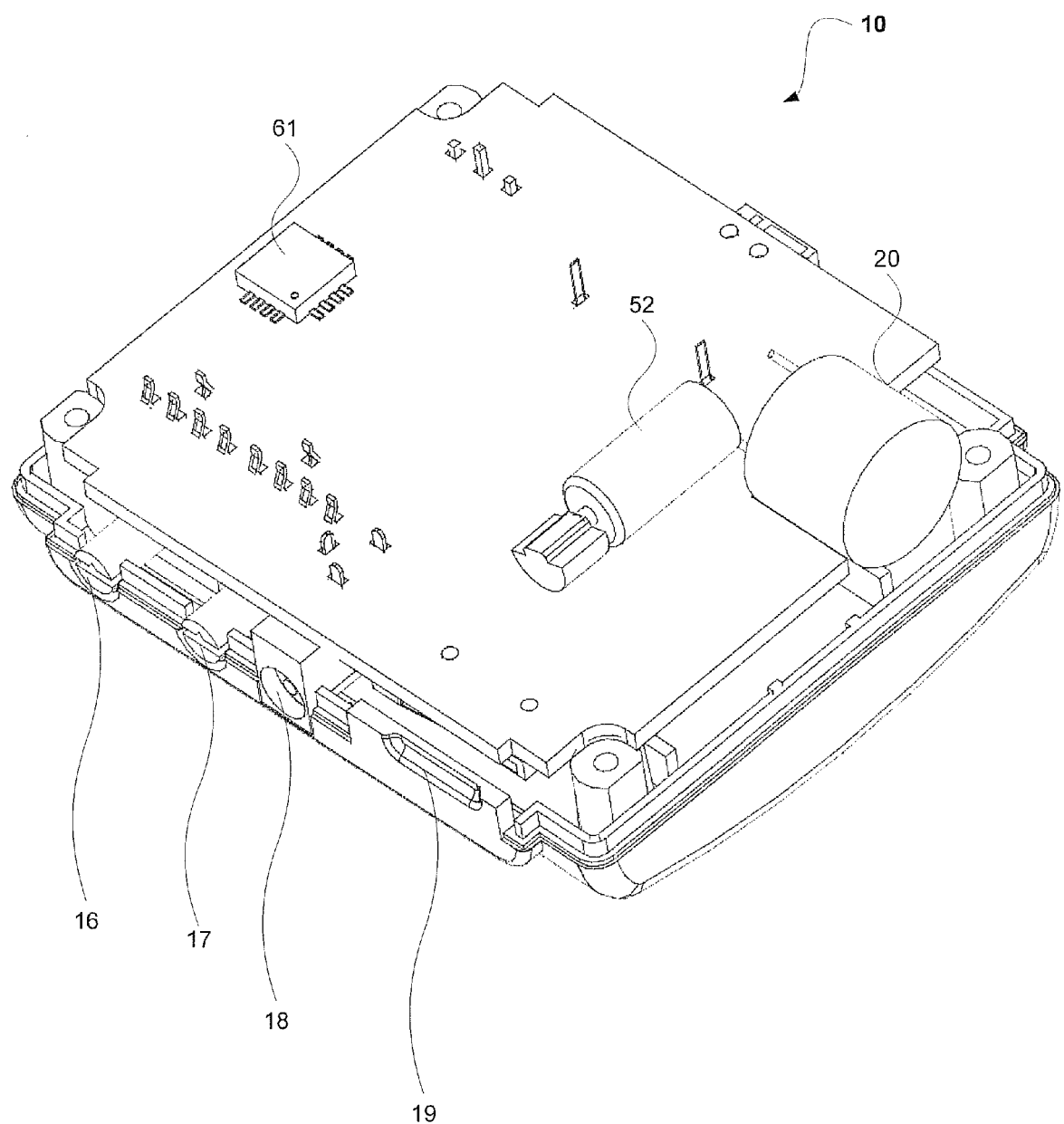
FIG. 6 is a perspective view from below of the device of FIG. 5 with a battery removed to show an accelerometer circuit.

Referring to FIGS. 1 to 6, a wearable portable device 10 for increasing awareness of a paretic limb to a user is provided. In one embodiment, the device 10 is provided in the form of a wristwatch and has a strap 11 to secure the device 10 to the wrist of the user. The device 10 generally comprises: a sensory signal generator 52, 20, a switch 13 and an accelerometer 61. The sensory signal generator 52, 20 emits a continuous sensory signal to remind the user to move the paretic limb according to a predetermined schedule. In one embodiment, the sensory signal generator is a vibrator 52 to generate a vibration. In a further embodiment, the sensory signal generator additional comprises a speaker 20 to generate a buzzing audible noise to accompany the vibration of the vibrator 52. The switch 13 is actuated by the user for stopping the emission of the sensory signal. The accelerometer 61 detects the movement of the paretic limb. After the switch 13 is actuated by the user, the user is instructed to move the paretic limb in accordance with predetermined instructions and the movement of the paretic limb detected by the accelerometer 61 and when the switch 13 is actuated are recorded for data analysis. Stroke patients are encouraged to perform regularly movement practices upon sensory cueing at home in addition to at the clinics. In order to monitor the compliance and recovery progress of users, the device 10 has a built-in acceleration measurement function to monitor arm movements and a removable memory card to record arm movement and the user's responses to sensory cues.

The sensory signal is continuously emitted according to a predetermined schedule or randomly before the switch 13 is pressed to stop it. The user must press the switch 13 as soon as possible after it has begun to emit the sensory cue as a method of avoiding conditioning. The emission of the sensory cue(s) is continuous until the switch 13 is pressed. In response to the signal, the user must move the upper extremity of their limb as instructed for five times after pressing the switch 13 to turn off the emission of the sensory cue. In other embodiments, the number of times the user must move their limb may vary. These pertinent sensory signals are provided to users to increase their awareness over the paretic limb. The device 10 may be set to emit a sensory signal in the form of a vibration cue simultaneously with an auditory cue in the form of a buzzing noise within a predetermined, variable or random time interval, for example, a few seconds to several minutes.

The switch 13 is relatively large and positioned in the middle of the top surface of the device 10. The switch 13 is an acknowledgement button for the user to press to stop the vibration but prior to being pushed also functions as a vibration visual indicator to visually indicate that vibration is occurring using a flashing blue LED backlight. An on/off button 15 for the device 10 is located below the switch 13. To avoid the user to accidentally pressing the on/off button 15 instead of the switch 13, the on/off button 15 has to pressed for five seconds in order to switch on or switch off. An LED indicator 14 is located adjacent to the on/off button 15 indicates whether the device 10 is on or off. The LED indicator 14 is dual color: red and green. When the battery 51 is being charged this is indicated by a red LED flashing at 2 Hz. When the battery 51 is fully charged this is indicated by a green LED flashing at 2 Hz.

On the side of the device 10, there is a vibration and sound selection rotary switch 16, vibration pattern selection rotary switch 17, DC power socket 18 and T-flash memory card slot 19.

The vibration and sound selection rotary switch 16 allows the user to configure the mode of sensory cueing, vibration or sound alone, or combination of both to be generated by the device 10 and whether vibration is to be generated also. The vibration pattern selection rotary switch 17 allows the user to configure the type of vibration to be generated, for example, various vibrating patterns, duration, strength of vibration, etc. The vibration interval may be 1 to 255 minutes (the default is 5 minutes) and the vibration pattern has an ON duration and an OFF duration in seconds. Minor adjustment of the parameters of the device 10 can be done by the rotary switches 16, 17 provided on the device 10.

The DC power socket 18 enables the 3.7V 450 mAh Li-ion rechargeable battery 51 to be recharged via mains power using a 5V DC power adapter plugged into the DC power socket 18. The battery charging status is illustrated by the red/green LED 14. The operational and recording capacity of the device 10 is up to 72 continuous hours.

The T-flash memory card slot 19 is for receiving a removable memory card which stores the recorded movement, time of movement, time of emission of the sensory signal, and time of actuation of the switch 16. The memory card may be a 16 MB or 2 GB MicroSD card. All raw data is recorded on the memory card. Movements and exercises of the patients are recorded in response to sensory cues. The real-time clock time-stamp and the acceleration measurements are recorded. The duration required by the patient to press the acknowledge button after a sensory cue has been initiated is also recorded. The memory card is later inserted into a computer to be read by data analysis software for review by a therapist or the user.

On the opposite side of the device 10, there is an RS232 interface 21 connector for setting the real-time clock in the device 10. After a USB driver is installed on a computer to enable communication between the device 10 and a clock setting software. When the device 10 connects to the computer via a cable using the RS232 interface 21, the real-time clock of the device 10 may be set Turning to FIGS. 4 and 5, within the casing of the device 10, the back-up battery 41 and rubber keys 42 are provided. The vibrator 52 to generate the vibration and a speaker 53 to generate sound are also provided. There is an aperture in the casing of the device 10 to enable the audio from the speaker 53 to be clearly heard. The vibrator 52 is able to vibrate at a speed of 11,000 RPM and the speaker 53 is able to generate a sound at 67 dB. The accelerometer 61 is a 3-axis accelerometer to detect motion of the limb that the device 10 is attached to.

The accelerometer 61 records the detected 3-axis motion onto the memory card. The amount of movement of the upper extremity of the limb per minute in X, Y and Z directions for users suffering from stroke is detected.

The mechanical specifications of the sensory cueing device 10 are that it is light weight, is a small size, and comfortable for prolonged wearing because the device 10 is worn on the patient's wrist for several hours daily. The top side of the device 10 is splash-proof to enhance durability. The strap 11 is made from non-allergic neoprene with a Velcro™ fastening mechanism to facilitate wearing with a single hand. Vibration cues of sufficient magnitude are required to stimulate the user. Large vibrations require more energy usage which depletes battery life. However, a larger battery may increase the overall weight of the device 10 and therefore a balance between power and weight considerations is chosen. Miniature components (such as a miniature vibration motor and battery) are necessary to provide the device 10 in a small form factor. Optimal energy saving strategies and optimising the space usage within the casing of the device 10 are important considerations that are embodied in the arrangement of components in the device 10 and also the energy usage pattern of the various electrical components.

The electrical components of the device 10 are an on/off button 15, LED 14 for on/off and low battery visual indication, internal speaker 20 for audio alerts, internal vibration motor 52 for vibration alerts. User configurable alert modes are provided which are: vibration only, vibration and audio, or none (motion logging only). The change of these three patterns can be done by adjusting switch 16. In order to avoid the switch 16 being easily changed, it is built on the same surface with the casing and needs a small screwdriver or small tool to adjust it. There is also data logging of: 3-axis motion by an internal accelerometer integrated circuit 61, and response time data. Other electrical components which have been described earlier include the T-flash memory card slot 19 for a removable memory card, an internal real-time clock configurable by the RS-232 connection 21, and the battery 51.

Figure 7:
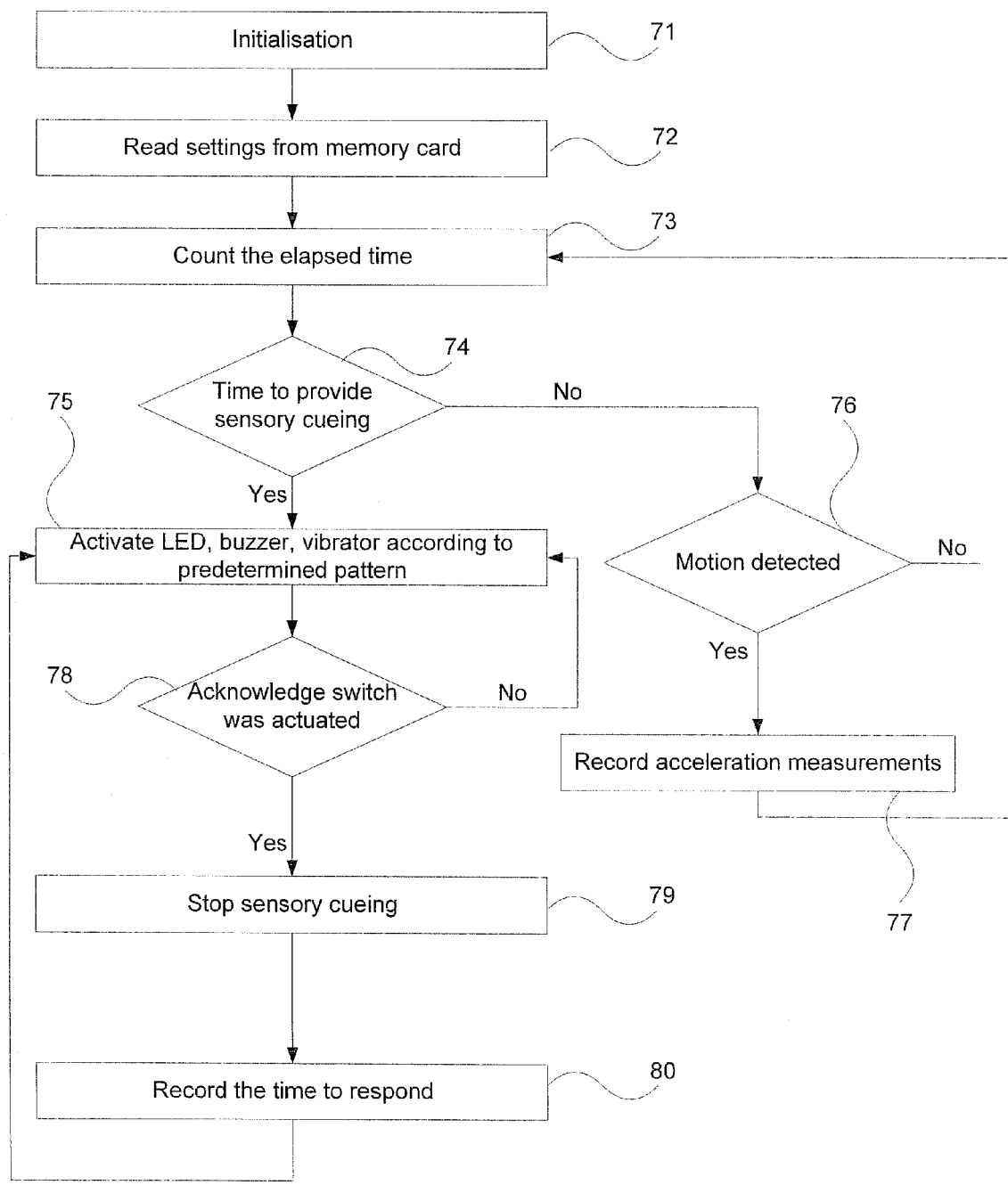
FIG. 7 is a process flow diagram depicted a method for increasing user awareness of a paretic limb in accordance with an embodiment of the present invention.

Referring to FIG. 7, a method for increasing user awareness of a paretic limb and recording the user awareness using the device is generally described. The device 10 is turned on by pressing the on button 15. The device 10 then performs its initialisation phase 71. Settings and parameters from the memory card inserted in the memory slot 19 are read. The time counter is activated and the elapsed time is counted 73 from the moment the device 10 is turned on. A schedule for sensory cueing is regularly checked or in an alternate embodiment there is no checking of a schedule if the device 10 is operating on a random basis for sensory cueing. If it is time to provide sensory cueing 74, the backlight LED for the switch 13 is activated 75, the buzzer 20 generates an audible sound and the vibrator 52 generates vibration in accordance with the user defined sensory cue parameters. The defined sensory cue parameters can be adjusted by adjusting switch 17. There are five pre-determined patterns by default but they can be changed by the software panel 85 depicted in FIG. 8. In order to avoid the switch 17 being easily changed, it is built in the same surface with the casting and need a small screwdriver or small tool to adjust it. Otherwise, the device 10 determines whether motion of the limb is detected 76. If no motion is detected, the device 10 returns to counting the elapsed time. If motion is detected, the acceleration measurements are recorded 77 onto the memory card to track the movement of the limb. After the sensory cue is emitted, the device 10 waits for the user to acknowledge the actuation of the switch 13. If there is no actuation of the switch 13, the sensory cue is emitted again. If the switch 13 is actuated, the sensory cueing is stopped 79. The time to respond to the sensory cueing by actuating the switch 13 is recorded 80 onto the memory card. The process is repeated until the user presses the off button 15.

The data analysis software reads and interprets the recorded data saved on the memory card in user-friendly graphs and summaries. All parameters of the device 10 may be pre-set using the software as depicted in FIG. 8. The vibration interval can be set in minutes 81. There are three parameters to configure the motion logging function: recording epoch 82, sampling rate 83 and data log enable/disable 84. The recording epoch 82 is the time interval to sense motion. The default setting is 2 seconds and it can be adjusted by the configuration file stored in the memory card. The sampling rate 83 is the logging frequency after a motion has been detected. Acceleration of movement is sampled at a range of 3 to 10 Hz and summed as a raw count over a user-specified epoch for a minimum of 1 second. The default setting is 10 Hz and it can be adjusted by the configuration file stored in the memory card. The data log enable/disable 84 is default to enabled and it can be adjusted by the configuration file stored in the memory card. The vibration patterns 85 can be created by choosing how many seconds on for the vibration and how many seconds off for the vibration. There are five different vibration patterns configurable that may be stored on the memory card. The user can also adjust a threshold filter to determine what level of body motion is to be recorded. Slight body motion may be disregarded as not constituting proper exercise of the paretic limb. The real-time clock on the device 10 can be set to the current local time. The time can be accurately recorded with the detection of movement and emission of the sensory signal.

Figure 9:
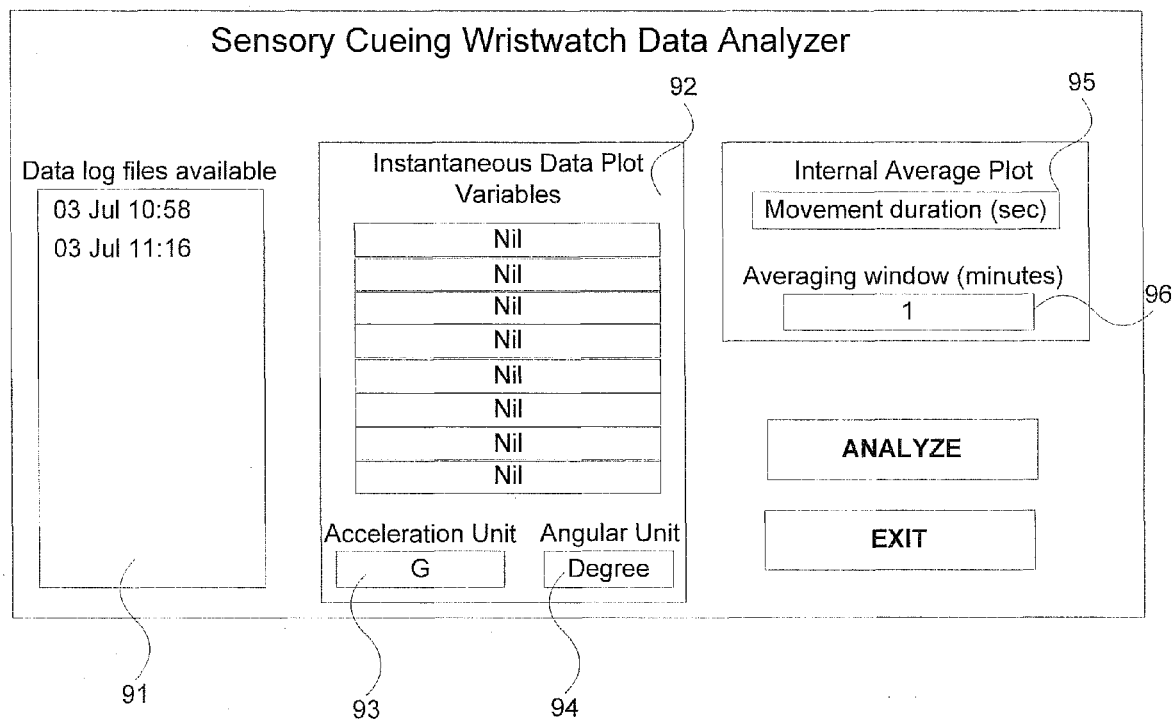
FIG. 9 is a screenshot from the data analysis software application to analyse the recorded data of the device of FIG. 1.
Figure 10:
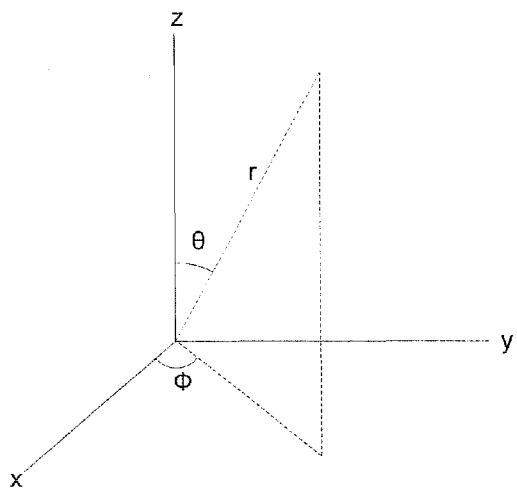
FIG. 10 is a spherical co-ordinate system used by the data analysis software application.
Figure 11:
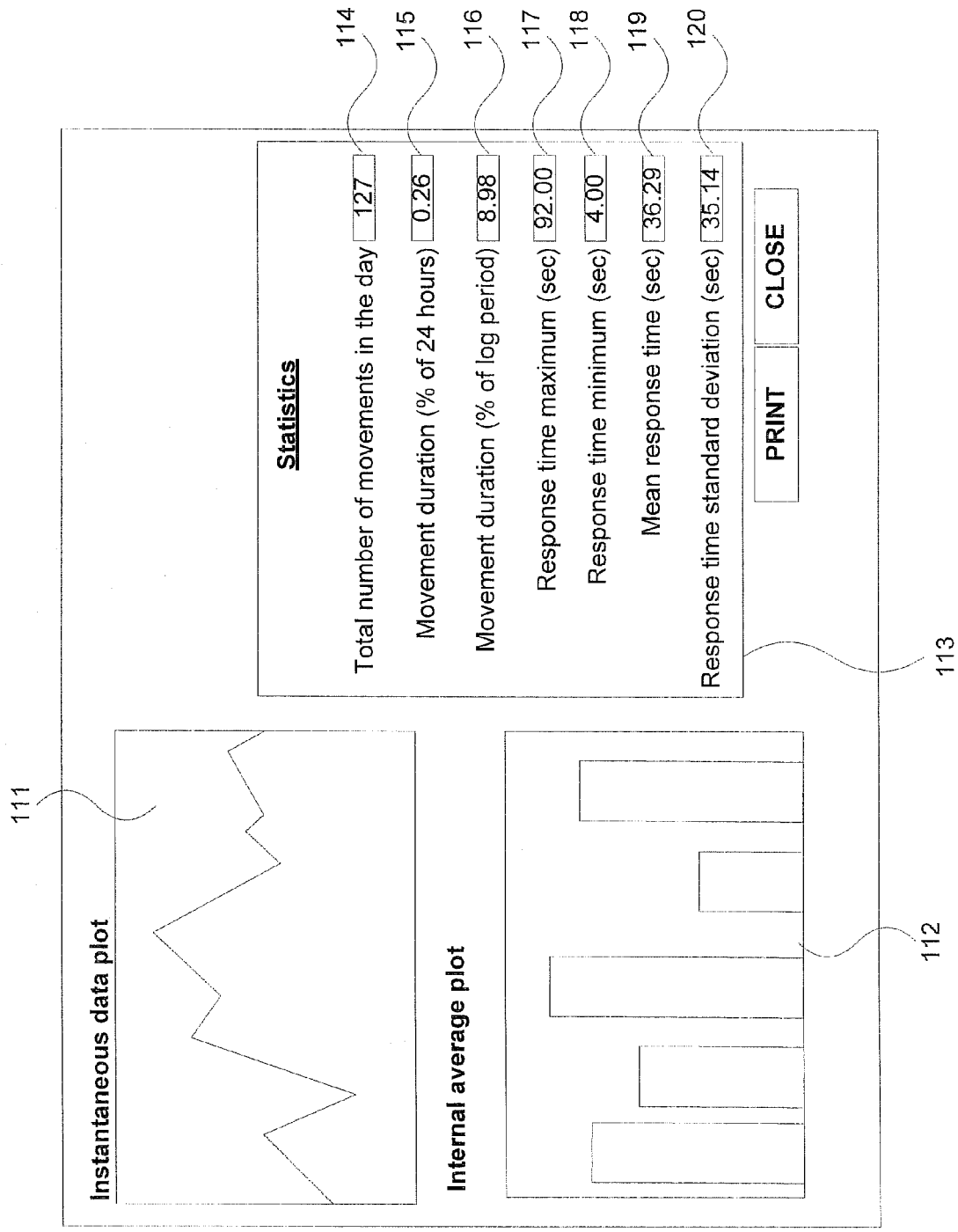
FIG. 11 a screenshot from the data analysis software application depicting a generated data analysis report using the recorded data of the device of FIG. 1.

Referring to FIGS. 9 to 11, the data analysis software enables visualization analysis of logged data. The software is a powerful and simple tool to allow therapists to view and analyze the data recorded. When stroke patients are able to practice independently and the progress can be monitored by the device 10, therapists can review each data log file 91 containing the recorded data to evaluate the recovery of the patients and to formulate appropriate treatment planning. The software enables raw data download from the device 10 and data visualization for interpretation by a therapist.

The data analysis software analyzes and visualizes the log data using three methods: Instantaneous data plot, interval average plot and statistics summary. In instantaneous data plot, all log data points recorded and the derived values can be displayed in graphs. This provides a detailed view of the log data for the therapists to look into the low-level details of arm motion and response time records. In interval average plot, the arm motion data are analyzed to find out the duration of arm movements in the interval window length specified. This provides a practical overview on when and how the patient moves and exercises his/her arms over the day. In statistics summary, the arm motion data and the response time data are analyzed to find out several major statistical values summarizing the patient's arm movement and response performance over the day. There are various parameters such as data plot variables 92, acceleration unit 93, angular unit 94, movement duration 95 and averaging window 96 that can be input into the data analysis software. The software also generates user-friendly charts 111 and graphs 112 for reporting and data analysis to a therapist. A summary of statistics 113 is also shown on a data analysis report generated by the data analysis software. For example, a physician may enquire how much the arm movement occurs in response to sensory cueing or how many times the arm is moved above a predetermined threshold during meal times.

For instantaneous data plot graph depicted on FIG. 11, there are 8 plots. It is possible to plot 10 variables in each plot. The acceleration units (G or ms-2) and the angular units (degrees or radian) may be selected. The 10 variables are: Nil, X, Y, Z, X+Y+Z, X–Y tilt, Y–Z tilt, X–Z tilt, X+Y+Z zenith (theta), X+Y+Z azimuth (alpha) and response time (seconds). The spherical co-ordinate system used in the data analysis software is depicted in FIG. 10 showing the X, Y and Z axes.

The data analysis software automatically calculates the following statistics of the arm movement and the response time:
1. Total number of movements in the day 114: This is the total number of continuous arm movements detected in one day.
2. Movement duration (% of 24 hours) 115: This is the total amount of time arm movement has been detected. It is expressed as a percentage of 24 hours.
3. Movement duration (% of log period) 116: This is the total amount of time arm movement has been detected. It is expressed as a percentage of the total amount of time the wristwatch has been turned on and has logged arm motion data during the day.
4. Response time maximum 117: This is the maximum value of response time measured.
5. Response time minimum 118: This is the minimum value of response time measured.
6. Mean response time 119: This is the mean value of response time measured.
7. Response time standard deviation 120: This is the standard deviation of response time measured.

The device 10 may be used for probing upper extremity functioning as well as reducing inattention over hemiplegic side in clients with stroke The sensory cueing is user-friendly. The device 10 provides several user-specified modes of sensory cueing including vibration, sound or any combination thereof with adjustable intensity and frequency. The sensory cues may be continuous or intermittent and are adjustable in duration according to the user's preference.

The device 10 provides autonomous treatment to stroke patients, with or without the neglect symptoms, at their home environment under guidance even in the absence of occupational therapists. This gives patients more time to practice detecting the hemiplegic side and exercising the hemiplegic arm, while the patient's conditions and compliance to treatment are monitored in an unattended manner.

The device 10 is intended to assist patients suffering chronic stroke to overcome learned non-use of the hemiplegic upper extremity. Target users include those with chronic stroke with both mild upper extremity impairments, without neglect symptoms so as to remind the patient of awareness of the paretic limb who have developed learned non-use. The device 10 may also be used for sensory and perceptual impairments and hand functions over both sides of the body, in a sample of post-stroke patient. Motor priming via the device 10 and motor training with only the use of motor training on levels of hand functions is possible. Functional imaging to understand the neural processes underlying the learning of the motor priming for modulating more balanced activities of the right and left sensory and motor cortices is also envisaged. This can show whether these are associated with improved motor performance after the motor system of the stroke patient has been primed.

Although the device 10 has been described as wrist worn, it may be attached to any limb of the person as required, for example, a foot. The strap 11 for the device 10 is adjustable to conform to various limb sizes.

Although vibration and sound have been described as sensory cues, other sensory cues are envisaged such as visual cues and temperature change. The user is instructed to move after cueing a predetermined pattern of movement voluntarily, however, it is envisaged that the movement can stop the cueing itself by a motion detection switch without using another limb to press off the switch 13.

Although a removable memory card has been described, it is envisaged in another scenario that the device 10 does not require a memory slot 19 but has an internal non-volatile memory for saving the recorded data. To transfer the recorded data to the data analysis software on a computer, a wireless communicator such as a WiFi transmitter or Bluetooth transmitter is provided in the device 10. Alternatively, a cable may be used to connect the device 10 to the computer for data transfer such as a USB cable. Advantageously, this may make the device 10 smaller in size by eliminating the need for a memory slot 19.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

I claim:

1. A wearable portable device for increasing user awareness of a paretic limb and recording the user awareness, the device comprising:
   a sensory signal generator configured to emit a continuous sensory signal to remind the user to move the paretic limb according to a predetermined schedule;
   a switch configured to be actuated by the user for stopping the emission of the sensory signal;
   an accelerometer configured to detect movement of the paretic limb in 3-axis; and
   a controller configured to, after the switch is actuated, provide instructions for moving the paretic limb and record the movement of the paretic limb detected by the accelerometer and response time of when the switch is actuated after the sensory signal is emitted.

2. The device according to claim 1, further comprising a non-transitory memory to store the recorded movement, time of movement, time of emission of the sensory signal, and time of actuation of the switch.

3. The device according to claim 1, wherein the sensory signal is a vibration output, audio output, visual output or a combination thereof.

4. The device according to claim 1, wherein the device is a wristwatch and further comprises an adjustable strap configured to fasten the device around the wrist of the user.

5. The device according to claim 2, including a computer for analyzing and interpreting the recorded movement, time of movement, time of emission of the sensory signal, and time of actuation of the switch, and for generating charts to illustrate how much movement of the limb occurs in response to the sensory signal and how many times the limb is moved above a predetermined threshold during a predetermined time interval.

6. The device according to claim 1, further comprising rotary switches configured to configure patterns, duration and intensity of the emission of the sensory signal.

7. The device according to claim 1, wherein parameters for the device including: vibration interval, epoch time, motion sampling rate, motion logging and vibration patterns are settable.

8. The device according to claim 1, wherein the switch is a button provided in a central location on an upper surface of the device.

9. The device according to claim 8, wherein the button is at least semi-transparent to enable an LED backlight positioned beneath the button to generate a visual indication of the emission of the sensory signal.

10. The device according to claim 2, further comprising a memory slot for the memory.

11. The device according to claim 1, further comprising a rechargeable battery configured to provide electrical power for the device.

12. A system for increasing user awareness of a paretic limb, the system comprising:
   a vibrating wrist-worn device configured to vibrate in order to remind the user to move the paretic limb according to a predetermined schedule, the device having a button configured to be pressed for stopping the vibration, and an accelerometer configured to detect movement of the paretic limb in 3-axis and the device configured to provide instructions to move the paretic limb in accordance with predetermined instructions; and
   a computer for analyzing the movement of the paretic limb detected by the accelerometer and response time of when the button is pressed after the vibration commences.

13. A method for increasing user awareness of a paretic limb, the method comprising:
   generating a sensory signal to remind the user to move the paretic limb according to a predetermined schedule;
   actuating a switch by the user for stopping the emission of the sensory signal; and
   detecting movement of the paretic limb in 3-axis;
   wherein after the switch is actuated by the user, the user is instructed to move the paretic limb in accordance with predetermined instructions and the movement of the paretic limb detected by an accelerometer and response time of when the switch is actuated after the sensory signal is emitted are recorded for analysis.

14. The method of claim 13, further comprising recording the reaction time to actuating the switch in response to the emission of the sensory signal.

\* \* \* \* \*